United States Patent [19]

McCracken et al.

[11] Patent Number: 4,614,183
[45] Date of Patent: Sep. 30, 1986

[54] ADHESIVE FILM DRESSING

[75] Inventors: Robert W. McCracken, North Brunswick; Linda A. Baesler, Chatham, both of N.J.

[73] Assignee: Johnson & Johnson Products, Inc., New Brunswick, N.J.

[21] Appl. No.: 735,306

[22] Filed: May 17, 1985

Related U.S. Application Data

[63] Continuation of Ser. No. 461,405, Jan. 27, 1983, abandoned.

[51] Int. Cl.⁴ .............................................. A61L 15/00
[52] U.S. Cl. ............... 128/132 R; 128/132 D; 128/156; 128/155
[58] Field of Search ............... 128/132 D, 132 R, 155, 128/156; 604/389, 390

[56] References Cited

U.S. PATENT DOCUMENTS 3,349,765 10/1967 Blanford ..................... 128/132 D
3,645,835 2/1972 Hodgson ..................... 128/132 D
4,245,630 1/1981 Lloyd et al. ..................... 128/155
4,372,303 2/1983 Grossmann et al. ........... 128/132 D

FOREIGN PATENT DOCUMENTS 2128479 5/1984 United Kingdom .

Primary Examiner—John D. Yasko
Assistant Examiner—Sherri E. Vinyard
Attorney, Agent, or Firm—Wayne R. Eberhardt

[57] ABSTRACT

A thin adhesive coated film dressing is provided with the adhesive surface covered by a release paper in three sections to facilitate the application of the dressing to the wound site. The construction of the dressing provides for the center section of the release paper to be removed to expose the central adhesive area of the film. While gripping the film by the two end portions still covered by the release paper, the central portion of the dressing is applied to the wound site. Once the center section is secure, the end sections of the release papers are removed and application of the dressing completed.

14 Claims, 7 Drawing Figures

ADHESIVE FILM DRESSING

This application is a continuation of application Ser. No. 461,405, filed Jan. 27, 1983 now abandoned.

FIELD OF THE INVENTION

This invention relates to dressings for medical and surgical applications and, more particularly, to thin, transparent, adhesive film dressings which are commonly used as wound coverings and to secure IV catheters.

BACKGROUND OF THE INVENTION

Thin, transparent polymeric film adhesive dressings are widely used in medical and surgical practice for a variety of applications and are offered to the profession in a variety of sizes and shapes. In IV catheterization procedures, film dressings about 2 to 4 inches square are useful to stabilize the catheter and prevent movement which could cause infiltration of bacteria or phlebitis. The transparency of the dressing permits constant visualization of the catheterization site and the dressing provides a barrier against bacterial invasion, helping to reduce the risk of infection. Such films are generally moisture-vapor permeable to permit the covered skin to breathe and reduce the possibility of maceration.

Film dressings are also useful in the prevention and care of skin ulcers. Before skin breakdown, film dressings provide physical protection by shielding the inflammed area from irritating fluids and bacteria. For superficial ulcers, film dressings maintain hydration of the wound surface providing an optimal environment for epidermal healing, while acting as a barrier to fluids and bacterial contaminants. For deeper ulcers, after appropriate therapy has eliminated infection and a healthy granulation bed has been established, the film dressings help maintain an optimal healing environment while protecting against contamination and permitting visualization of the wound site without dressing change. The films for use as ulcer dressings are typically from about 4 inches square to about 8 by 10 inches in size.

Larger sized film dressings from 12 by 20 inches or greater are useful as surgical incise drapes. The film is placed over the area to be incised and the incision is made through the transparent film. The use of an incise drape provides a sterile field immediately surrounding the operative site.

Thin, transparent, adhesive polymeric films for surgical application having a thickness of from about 20 to 75 microns and preferably from about 30 to 45 microns are fabricated from polyurethanes such as Goodrich ESTANE polyurethane, elastomeric polymeric esters such as DuPont HYTREL polyester elastomer, and blends of polyurethane and polyester elastomers. Polyurethane and elastomeric polyester films which are moisture vapor permeable and sufficiently elastic to conform to various body contours are particularly preferred for use in surgical applications.

The films are coated on one surface with a medical grade, pressure-sensitive adhesive using standard coating techniques. The adhesive is protected with a covering of a release paper or other backing material which can be readily removed at the time of use.

Releasable backing materials include films of polyethylene, polypropylene and fluorocarbons and papers coated with these materials or with silicone release agents. Examples of silicone-coated release papers are POLYSLIK supplied by H. P. Smith Co., and offered in various formulations to control the degree of adhesion of the paper to the adhesive surface.

Because of the thinness and flexibility of the polymeric film, the material is difficult to handle once the protective covering is removed from the adhesive surface, especially in the larger sizes. If the dressing folds so that the adhesive surfaces contact each other, it is difficult to separate and the dressing usually has to be discarded. In addition, the dressing is initially sterile for medical applications and touching the adhesive surface creates contamination sites under the dressing unless aseptic precautions are followed.

The prior art has proposed various methods for handling polymeric film dressings. For example, the nonadhesive surface of the film may be covered by an adherent liner which is die cut to form an inner portion in combination with a surrounding border portion as described in European Patent Application No. 81-304,905.3. When the adhesive release paper and the inner portion of the surface liner are removed, the border portion of the surface liner supports the film while it is being positioned on the patient, after which the border portion is removed. While such a construction offers the advantage of being able to position the dressing properly, it has other disadvantages such as the dressing cannot be applied under tension if required because of the restraining effects of the border paper. Additionally, removing the border paper from the film can cause the dressing to lift from the skin surface, in which case the user may touch the adhesive surface of the dressing during the final stages of application.

It is accordingly an object of the present invention to provide a thin, transparent film dressing having improved handling properties. It is a further object to provide a film dressing having a protective covering of the adhesive surface in a novel configuration which permits the film to be readily applied to the patient. It is a yet further object of the present invention to provide an adhesive film dressing which can be applied to a patient without touching the adhesive surface of the film. These and other objects of the present invention will be apparent from the ensuing description and claims.

SUMMARY OF THE INVENTION

A thin, polymeric film adhesive dressing is provided with the adhesive surface covered by a release paper having a central portion and two end portions. Each end portion has an edge flap adjacent the center portion folded back away from the adhesive surface to provide a means for readily gripping the release paper to remove it from the adhesive surface of the film. The center portion of the release paper has at least one edge flap adjacent an end portion extending over the end portion or folded back away from the adhesive surface of the film.

The film dressing is applied by first removing the center portion of the release paper and positioning the exposed center portion of the dressing over the application site while gripping the dressing by the two end portions. Each end portion of the release paper typically covers approximately 10 to 30 percent of the adhesive surface. The support provided by the end portions aids in preventing the dressing from folding in upon itself when the center portion of the release paper is removed. The dressing may be stretched if desired and readily positioned over the application site while being gripped by the end portions. Once the center portion is adhesively secured to the patient, the release papers are sequentially removed from the end portions while securing the end portions of the dressing.

DETAILED DESCRIPTION OF THE INVENTION

The thin film dressings of the present invention comprise a polymeric film having a thickness of from about 20 to 75 microns and preferably from about 30 to 45 microns coated on one surface with a pressure sensitive adhesive, and a removable protective material such as release paper covering the adhesive surface of the film.

Figure 1:
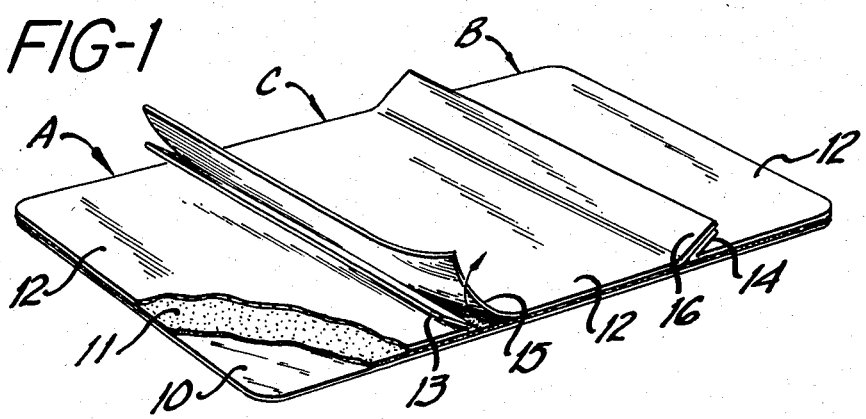
FIG. 1 is a view in perspective of a film dressing according to the present invention.

Referring now to FIG. 1, there is illustrated in perspective from the adhesive side of the film one embodiment of a dressing according to the present invention. As illustrated in partial section, film 10 is coated with adhesive 11 over one surface thereof, and the adhesive is covered by release paper 12 in three portions indicated as A, B, and C. Portion A extends from one end of the film and covers approximately 25 percent of the film area. Edge flap 13 of portion A is folded back from the adhesive surface and provides a means for gripping the release paper at the time of its removal.

At the opposite end of the film, release paper portion B covers approximately 25 percent of the film area and has edge flap 14 folded back from the adhesive surface. Intermediate to release paper portions A and B is central portion C which covers the approximately 50 percent remaining surface area of the film and is provided at either end with edge flaps 15 and 16 not adhered to the adhesive surface of the film.

Figure 2:
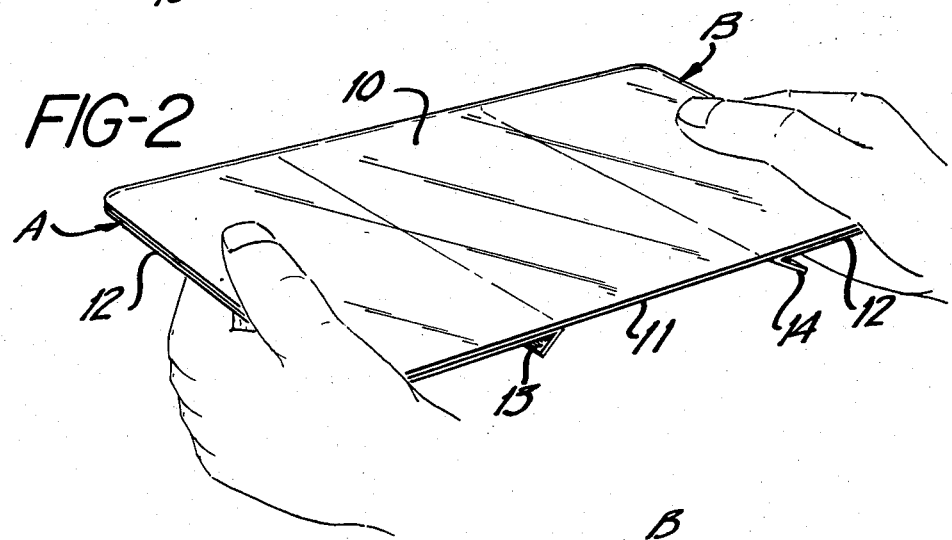
FIG. 2 is a view in perspective of the film dressing of FIG. 1 with the release paper removed from the center portion of the film.

Release paper C is removed from the central portion of the film dressing by grasping either edge flap 15 or 16 and removing the paper while holding the dressing by the adjacent end portion A or B respectively. Once the center release paper has been removed and discarded, the dressing is gripped in two hands over portions A and B as illustrated in FIG. 2. In this position, the dressing may be stretched if desired, and placed in position on the patient while viewing the placement site through the transparent center portion of the dressing.

Figure 3:
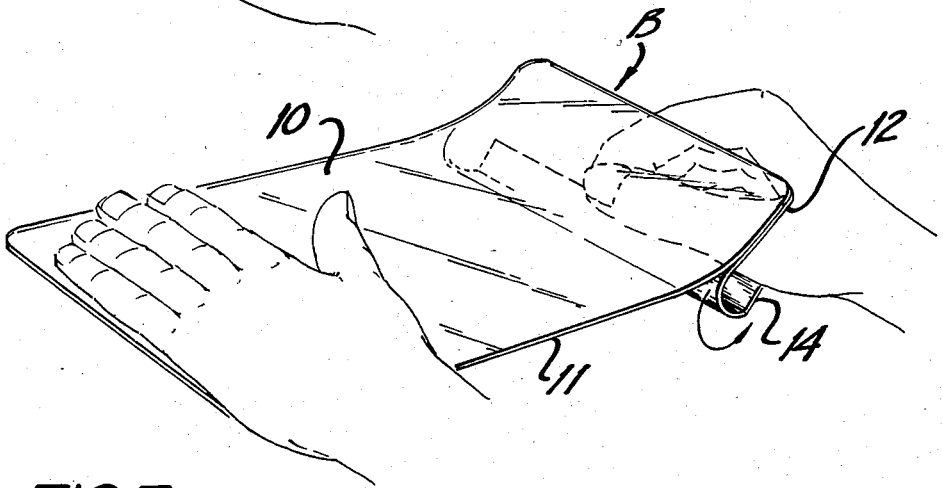
FIG. 3 is a view in perspective of the film dressing of FIG. 2 with the release paper from one end portion being removed after the center and other end portions have been secured to the patient.

Once the center portion of the dressing has been secured, the release paper of each end portion is removed in turn by grasping end flaps 13 and 14 and withdrawing the release paper while pressing downward on the film to secure the adhesive attachment of the end portion to the patient as illustrated in FIG. 3.

Adhesive film dressings of the present invention are easily handled, readily positioned on the patient in a taut, wrinkle free condition. Moreover, the dressings may be applied without touching or contaminating the adhesive surface of the film.

Figure 4:
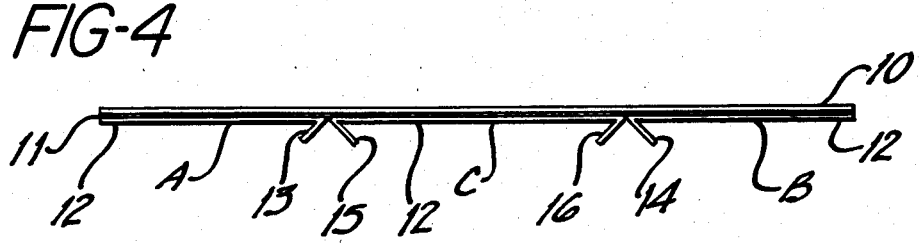
FIG. 4 is a side edge view of one embodiment of a film dressing according to the present invention.

Various embodiments of the dressings of the present invention are illustrated in FIGS. 4, 5, 6 and 7. In FIG. 4, the dressing which corresponds to that of FIG. 1 is characterized by the center release paper portion having two edge flaps 15 and 16 adjacent the end portions A and B respectively. In this configuration, center portion C may be removed beginning from either end.

Figure 5:
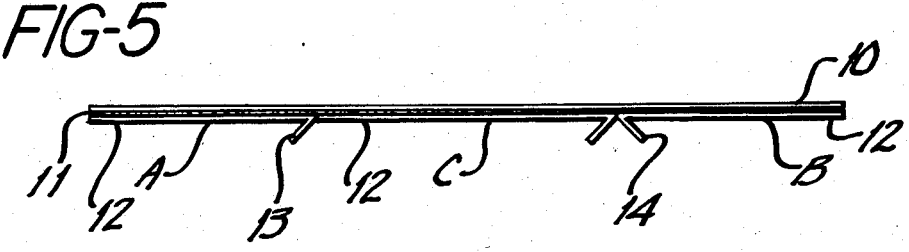
FIG. 5 is a side edge view of a second embodiment of a film dressing according to the present invention.

In FIG. 5, the release paper center portion C is provided with a single edge flap 16 adjacent end portion B. In this configuration, center portion C is readily removable only beginning from end B. In FIGS. 4 and 5, the edge flaps of all release paper portions are folded well back from the adhesive surface at an acute angle to permit the edge flaps to be readily grasped to remove the release paper.

Figure 6:
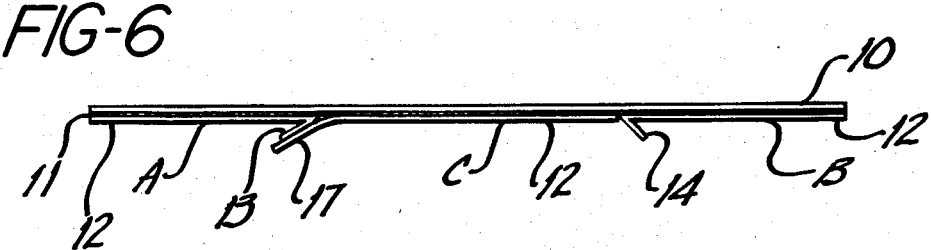
FIG. 6 is a side edge view of a third embodiment of a film dressing according to the present invention.

In FIG. 6, the release paper of center portion C is provided with a single edge flap 16 which overlies edge flap 13 of portion A, but extends slightly beyond edge flap 13 to permit edge flap 17 to be individually grasped when the center portion of the release paper is to be removed.

Figure 7:
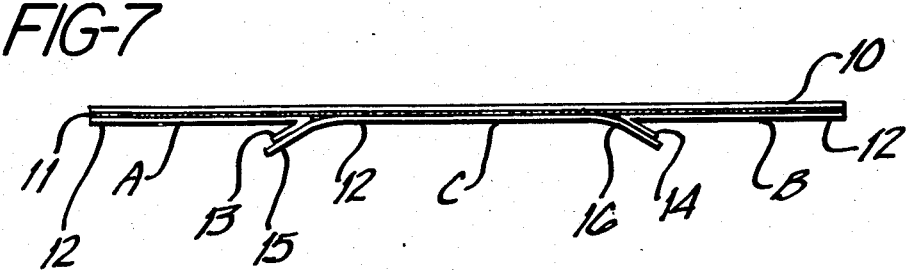
FIG. 7 is a side edge view of a fourth embodiment of a film dressing according to the present invention.

In FIG. 7, edge flaps 13 and 14 of the end portions of the release paper are folded back substantially 180° and the release paper of center portion C overlies and extends slightly beyond edge flaps 13 and 14. The advantage of the dressing configuration illustrated in FIG. 7 is that the release papers lie flat against the adhesive surface of the dressing, and the resulting dressing is easier to package and the packages are less bulky.

In a preferred embodiment of the present invention, end portion release papers A and B require a slightly greater pull off force than the release papers of center section C. The pull off force of the paper for any given adhesive surface is determined by the composition of the silicone coating on the release paper and various papers having greater or lesser release levels are commercially available. In the case of the present invention, the pull off value of the center portion release paper is preferably from about 0.4–0.7 ounces per inch (4.5–7.8 grams per centimeter) while the pull off value of the end portion end portion release paper is preferably from about 0.8–1.1 ounces per inch (8.9–12.2 grams per centimeter).

The pull off values are determined according to ASTM D-3330-76 by removing the release paper from a one inch (2.54 centimeter) wide strip of adhesive film at a rate of 12 inches per minute (30.5 centimeters per minute) in an instrument such as an Instron Tensile Tester wherein the film and release paper are gripped in opposing jaws, and the restraining force measured while the jaws are separated at a constant rate.

The advantage of having higher pull off values for the end portions of the release papers is particularly significant in connection with the larger sized films due to the film placement technique as illustrated in FIG. 3. Once the center portion of the film has been applied, the end portions are secured by pulling off the release paper while pressing downward on the film. The higher pull off forces provide better control in securing the end portions of the film and also impart tension to the film to prevent wrinkles. Since the release paper in the center portion of the film is completely removed before the film is applied, lower pull off values for this portion are preferred although higher values may be used without serious disadvantage.

The dressings of the present invention are prepared using standard surgical dressing manufacturing techniques wherein a supply of film is coated with the desired medical grade, pressure-sensitive adhesive, and the releasable backing material is applied to the adhesive surface. The end portions of the backing material are applied first with the edge flaps folded back from the adhesive surface as hereinbefore described. The center portion of the backing material is subsequently applied with one or both edges overlying the end portions. Individual dressings are die cut from the resulting continuous feed of laminated material, and packaged and sterilized prior to use following conventional procedures.

The present invention is directed to providing conventional thin film polymeric dressings with an improved release paper system covering the adhesive surface in order to facilitate the application of the dressing to the patient. Various modifications of the release paper system herein described including variations in materials and dressing configurations, will be apparent to those skilled in the art, and such modifications are included within the spirit and scope of the present invention.

What is claimed is

1. In a thin film surgical dressing comprising a thin polymeric film having on one surface a continuous coating of pressure sensitive adhesive, the improvement comprising covering the adhesive coated surface with three sections of backing material adapted to be removed from the dressing at the time of application, said sections of backing material comprising a center portion and two end portions, each of said end portions of said backing material having an edge flap adjacent the center portion folded back from the adhesive surface of said dressing, and the center portion having at least one edge flap adjacent an end portion positioned away from the adhesive surface of said dressing whereby said center portion of said backing material is readily removable before application of said dressing to a patient, and said end portions of said backing material are readily removable after the center portion of said dressing has been adhesively secured to said patient.

2. A dressing of claim 1 wherein said backing material comprises a silicone coated release paper.

3. A dressing of claim 1 wherein said backing material comprises a polyethylene film.

4. A dressing of claim 1 wherein said end portions of said backing material cover up to about one third of said dressing surface and said center portion covers at least about one third of said dressing surface.

5. A dressing of claim 4 wherein said center portion comprises approximately one half the area of said dressing surface.

6. A dressing of claim 1 wherein said edge flaps of the end portions of said backing material are folded away from said adhesive surface of said dressing.

7. A dressing of claim 6 wherein the end flaps of each of said end portions are folded back away from said adhesive surface, and said center portion overlaps at least one of said folded back end flaps.

8. A dressing of claim 1 wherein the force to remove said backing material from said end portions is greater than that required to remove said backing material from said center portion.

9. A dressing of claim 8 wherein the force to remove said backing material from said end portions is at least about 9 grams per centimeter.

10. A dressing of claim 8 wherein the force to remove said backing material from said end portions is from about 8.9 to 12.2 grams per centimeter, and the force to remove said backing material from said center section is from about 4.5 to 7.8 grams per centimeter.

11. A dressing of claim 1 wherein each of said end portions of said backing material have an edge flap adjacent the center portion folded back substantially 180°, and the backing material of said center portion has edge portions overlying and extending beyond said edge flaps of said end portions.

12. A dressing of claim 1 wherein said thin polymeric film comprises a polyether-polyurethane having a thickness of from about 20 to 75 microns.

13. A dressing of claim 12 wherein said film has a thickness of from about 30 to 45 microns.

14. A dressing of claim 1 contained in a sterile package.

* * * * *